(12) United States Patent
Schnitzler et al.

(10) Patent No.: US 8,154,795 B2
(45) Date of Patent: Apr. 10, 2012

(54) STEREO MICROSCOPE WITH BEAM SPLITTER DEVICE

(75) Inventors: Harald Schnitzler, Lüchingen (CH); Peter Strobel, Grub (CH); James Ng, Singapore (SG); Manfred Kuster, Widnau (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 12/428,148

(22) Filed: Apr. 22, 2009

(65) Prior Publication Data
US 2009/0268281 A1 Oct. 29, 2009

(30) Foreign Application Priority Data
Apr. 23, 2008 (DE) .................. 10 2008 001 352

(51) Int. Cl.
*G02B 21/22* (2006.01)
(52) U.S. Cl. ........................ 359/384; 359/376
(58) Field of Classification Search ........... 359/372–378
See application file for complete search history.

(56) References Cited

U.S. PATENT DOCUMENTS

| | | | | |
|---|---|---|---|---|
| 4,035,057 A * | 7/1977 | Klein | ............. | 359/384 |
| 4,991,947 A | 2/1991 | Sander et al. | | |
| 5,552,929 A | 9/1996 | Fukaya et al. | | |
| 5,668,661 A * | 9/1997 | Tomioka | ............. | 359/380 |
| 6,421,173 B1 * | 7/2002 | Corbisiero et al. | ............. | 359/372 |
| 2002/0159157 A1 * | 10/2002 | Deverin et al. | ............. | 359/629 |
| 2003/0112509 A1 * | 6/2003 | Takahashi | ............. | 359/466 |
| 2003/0133187 A1 | 7/2003 | Schmidt et al. | | |
| 2004/0105147 A1 * | 6/2004 | Hermann et al. | ............. | 359/374 |
| 2004/0120031 A1 * | 6/2004 | Fukaya et al. | ............. | 359/375 |
| 2004/0252371 A1 | 12/2004 | Sturgis et al. | | |
| 2006/0215258 A1 * | 9/2006 | Strobel et al. | ............. | 359/368 |
| 2008/0100893 A1 | 5/2008 | Knuenz et al. | | |

FOREIGN PATENT DOCUMENTS

| | | |
|---|---|---|
| DE | 195 04 427 B4 | 9/1995 |
| DE | 101 57 613 A1 | 10/2002 |
| DE | 10 2006 050 846 A1 | 5/2008 |
| EP | 0 363 762 B1 | 4/1990 |
| EP | 1 308 766 B1 | 5/2003 |
| EP | 1 486 813 A1 | 12/2004 |

* cited by examiner

*Primary Examiner* — Mark Consilvio
(74) *Attorney, Agent, or Firm* — Foley & Lardner LLP (57) ABSTRACT

The present invention relates to a stereo microscope (20) with a first and a second main beam path (21, 22), the spacing of which defines a stereo base (23), wherein an axis of the microscope (24) extends through the middle of the stereo base (23) parallel to the main beam paths (21, 22), and with an optical beam splitter device (30) for producing an assistant beam path (31) and a documentation beam path (32), wherein the direction of the assistant beam path (31) in a first position is rotated by 180° to the direction of the assistant beam path (31) in a second position of the beam splitter device (30), and the decoupled documentation beam path (32) in both positions of the beam splitter device (30) is in each case perpendicular to the decoupled assistant beam path (31), and wherein in both the first and second positions of the beam splitter device (30) the assistant beam path (31) can in each case be decoupled at least from the first main beam path (21) and the documentation beam path (32) can in each case be decoupled at least from the second main beam path (22).

10 Claims, 5 Drawing Sheets

STEREO MICROSCOPE WITH BEAM SPLITTER DEVICE

CROSS-REFERENCE TO RELATED PATENT APPLICATIONS

The right of foreign priority is claimed under 35 U.S.C. §119(a) based on Federal Republic of Germany Application No. 10 2008 001 352.8, filed Apr. 23, 2008, the entire contents of which, including the specification, drawings, claims and abstract, are incorporated herein by reference.

BACKGROUND OF THE INVENTION

The present invention relates to a stereo microscope having a first and a second main beam path, the spacing of which defines a stereo base, while extending through the middle of the stereo base, parallel to the main beam paths, is a microscope axis, and having an optical beam splitter device for producing an assistant beam path and a documentation beam path.

Stereo microscopes of this kind are used particularly in opthalmological and neurosurgical operations. In such cases a binocular tube is provided downstream of the beam splitter device, and through this the surgeon or main operator can observe the object stereoscopically. Stereo microscopes of this kind may be of a telescope type (Galileo system) where a main objective common to both main beam paths is mounted on the microscope body. Stereo microscopes of the Greenough type are also known, in which one objective is provided for each main beam path. Often, a magnification changer or a zoom system is provided downstream of the objective. In this way it is possible to achieve different fixed magnifications or a continuous magnification range. One channel of a magnification changer (zoom system) is provided for each of the two channels (main beam path) of the stereo microscope, while the two magnification changer/zoom system channels are to be adjusted or moved in synchronism. In a structure of this kind, the above mentioned beam splitter device is expediently mounted downstream of the magnification changer/zoom system. Stereo microscopes of this kind are sufficiently well known and need not therefore be discussed in detail at this point.

When a stereo microscope of this kind is used as a surgical microscope, an assistant beam path is frequently coupled out (blanked out) from one of the two or from both main beam paths and deflected to an interface for an assistant tube, and the assistant or co-observer is able to view an image of the object through this assistant tube. When the assistant beam path is coupled out from only one of the two main beam paths, a monoscopic (non-three dimensional) image is obtained. However, in the assistant tube, an assistant beam path of this kind can be split into two channels (of smaller stereo base), thus producing a stereoscopic image with a reduced three dimensional impression. Furthermore, it is expedient and known to couple out a documentation beam path which is fed to a documentation module or documentation device. These documentation modules may be, for example, opto-electrical receivers (CCD arrays) or other image memories which are able to receive and store sequences of images or individual images. By means of documentation devices of this kind it is possible, for example, to determine the progress of an operation for documentation purposes or to store individual images of the object for later analysis.

It should be pointed out in this connection that the terms "assistant beam path" and "documentation beam path" have been chosen purely for an easier understanding of the use of the stereo microscope according to the present invention and may be replaced by the general terms "secondary beam path" or "tertiary beam path", if these beam paths are to be used in some other way. In the description that follows, for the sake of simplicity, the terms assistant and documentation beam paths will be used without restricting the invention to a stereo microscope having corresponding assistant or documentation modules.

In the surgical microscopes mentioned above it is desirable to place the assistant or co-observer on the left or right hand side of the microscope, as desired. For this purpose, it is known to couple out an assistant beam path from the left and also from the right main beam path and lead it to a corresponding interface on the microscope housing. However, if the corresponding microscope is equipped with only one assistant tube, this tube has to be transferred from one side to the other if there is a change of assistant. Such modification is a source of risks and sterility problems. The provision of two fixed assistant tubes would be an adverse step for reasons of weight and cost.

There are also solutions in which the assistant tube is constructed to be pivotable in a horizontal plane. The horizontal plane here is a plane which is perpendicular to the plane containing the two main beam paths of the stereo microscope. These solutions require two additional assistant main beam paths extending parallel to the two stereo main beam paths, resulting in a complex four-beam microscope construction. A further disadvantage of such solutions is that the main observer tube has to be removed or at least moved out of the way before the assistant tube can be pivoted.

From EP 1486813 A1, a stereo surgical microscope with an assistant tube is known which is pivotably mounted on the rear side of the microscope in a plane parallel to the stereo main beam paths. The main observer tube is arranged on the front of the microscope. The assistant tube leads backwards and outwards from the rear of the microscope and depending on the desired position of the assistant it can be pivoted from the left hand side to the right and back again. The output coupling of a documentation beam path is not discussed here. In an arrangement of this kind, for reasons of stability, it is advantageous to mount a counterweight on the pivotable assistant tube. This has proved disadvantageous in practice, however, for reasons of cost, weight and adjustment.

From D E 19504427 B4, a stereo microscope is known having a single optic, i.e. with only one channel, in which a beam splitter element is provided downstream of the main objective and a magnification changer. The beam splitter element couples a secondary observation beam path out from the primary observation beam path. The beam splitter element consists of three separate prisms. Downstream of the beam splitter element are provided two optical elements arranged adjacent to one another which provide an intermediate image of the object under consideration, detected by two opto-electronic picture receivers. A construction of this kind is suitable for a video stereo microscope. The secondary observation beam path is also imaged on a picture receiver of this kind. The entire optics of the secondary observation beam path including the beam splitter element are mounted to be rotatable about a rotation axis which extends through the pupil used jointly by the primary and secondary observation beam path. This proposed construction is unsuitable for a two-beam stereo microscope. The beam splitter element here rotates about a correspondingly broad channel of the main beam path. Moreover, this specification does not discuss the output coupling of a further tertiary or documentation beam path.

Finally, from U.S. Pat. No. 5,552,929, a stereo microscope is known having a main observer tube, a co-observer tube and a documentation output. This is also a so-called "single optical system" in which the splitting into two beam paths takes place for the first time in the tube. The output coupling of the beam paths into one beam path for the main and co-observer is carried out by means of beam splitters arranged in a correspondingly broad channel of the main beam path. The construction proposed therein is unsuitable for two-beam stereo microscopes as any pivoting of a tube in such microscopes would cause the image to rotate as well. Consequently, prisms again have to be provided which will turn the image back again. A similar system, albeit without a documentation output, is known from EP 0363762B1.

In other known two-beam stereo microscopes, hitherto a so-called "semi-" stereo assistant has been attached to the side of the beam splitter. The latter is not pivotable as the (video) documentation is already connected on the opposite side, to which the second main beam path is fed. The impossibility of changing the assistant is highly disadvantageous for users in this case. Other solutions already mentioned use a four-beam microscope structure resulting in stereo microscopes in a substantially higher price bracket.

EP 1308766B1 relates to an operating stereo microscope with two first beam splitters in the two main beam paths which couple out part of the observation beam path to video cameras which are viewed to the left and right of the main observer. Using beam deflector elements, a further part of the light of the observation beam path is guided to a main observer tube, whilst the other part is guided to a co-observer tube arranged opposite the main observer tube. In order to afford the assistant the possibility of looking into the microscope to the side (i.e. to the left or right) of the main observer, a reflection device which is rotatable through 90° is provided, which deflects the assistant beam path accordingly. In this case, the only one documentation connection is then located opposite the assistant and to the side of the main observer.

From DE 10157613A1, different arrangements of a surgical microscope are disclosed, in which either the co-observer is positioned opposite the main observer, in which case the co-observer sees a stereoscopic image, or the co-observer is positioned to the side of the main observer, in which case the co-observer views the microscopic image in monoscopy. Beam paths for a documentation device are not envisaged here.

Moreover, a stereo microscope having a beam splitter device of the kind described herein before is known from the German Patent Application DE 102006050846.7 by the present Applicant, entitled "Stereo Microscope With Beam Splitter Device", which was filed before the filing date but had not yet been published on the filing date of the present application. In this prior application, in a first position of the beam splitter device, the assistant beam path can be coupled out of the first main beam path and in a second position can be coupled out of the second main beam path and the documentation beam path can be coupled out of the other main beam path in each case. The direction of the assistant beam path in the first position of the beam splitter device to the direction of the assistant beam path in the second position of the beam splitter device is rotated through 180° and the coupled out documentation beam path in both positions of the beam splitter device is perpendicular to the coupled out assistant beam path. By comparison with the subject-matter of the earlier application, the present application seeks to manage with a lower number of movable elements, thereby simplifying manufacture and assembly and consequently reducing costs.

SUMMARY OF THE INVENTION

One object of the present invention is therefore to provide a stereo microscope having a two-beam structure and an optical beam splitter device for producing an assistant beam path and a documentation beam path, with which an easy change of assistant is possible and the number of movable elements is low.

This object is satisfied by a stereo microscope as described herein.

A stereo microscope of the kind described herein before is proposed, in which an optical beam splitter device is provided for producing an assistant beam path and a documentation beam path, the direction of the assistant beam path in a first position being rotated through 180° relative to the direction of the assistant beam path in a second position of the beam splitter device, and the coupled out documentation beam path in both positions of the beam splitter device being perpendicular to the coupled out assistant beam path, and wherein, in the first and second positions of the beam splitter device, the assistant beam path is in each case adapted to be coupled out (at least) from the first main beam path and the documentation beam path is in each case adapted to be coupled out (at least) from the second main beam path.

Consequently, in the stereo microscope according to the invention, the documentation beam path is, also during a change of assistant, always coupled out from the same (second) main beam path. Analogously, the assistant beam path is always coupled out from the same other one of the two main beam paths when there is a change of assistant. In both cases, consequently, monoscopic or stereoscopic observation with a reduced 3-dimensional impression of the image is possible. In another embodiment which will be described in more detail hereinafter, the assistant beam path may be coupled out from both main beam paths. This theoretically provides the possibility of stereoscopic observation. The beam splitter device is constructed so that (at least) two different positions can be adopted in which the assistant beam path is rotated through 180° in order to allow a change of assistant. As the coupled out documentation beam path in both cases is perpendicular to the coupled out assistant beam path, a change of assistant of this kind is possible without the risk of collision with the interface for the documentation, as the latter may for example be mounted on the back of the stereo microscope, whereas the interface for the assistant is located for example on the right and left of the microscope housing. If this interface is designed to be pivotable, the pivoting may take place over the front of the microscope. As the assistant beam path is always able to be coupled out from one of the main beam paths and the documentation beam path can always be coupled out from the other main beam path, i.e. in both positions of the beam splitter device, the brightness conditions for the main observer, the assistant and documentation remain the same when there is a change of assistant.

The structure of a stereo microscope according to the invention may correspond to the structure which is already known and described above, apart from the beam splitter device. The description that follows, without restricting the generalities, sets out from a structure having a main objective, which is conventionally followed by a magnification changer or zoom system with two channels which define the two main beam paths, the beam splitter device being adjacent to the magnification changer/zoom system. Downstream may be provided a binocular tube for stereoscopic viewing of the object and/or a connection for a documentation module for (opto-electronic) documentation of the object viewing. This binocular tube is normally used by a main observer (surgeon). To simplify the description that follows it will be assumed that the main observer is situated at the front of the microscope, that the interface for the documentation is arranged at the back of the microscope and advantageously an interface to an assistant module is provided which is located in a housing that is rotatable through at least 180° about the axis of the microscope. However, it should be pointed out that the invention can also be implemented if two opposing interfaces to an assistant module are provided (for example on the left and right of the microscope housing). It would, however, be disadvantageous in a solution of this kind if there were a need to dismantle and assemble an assistant tube or a need for two fixed assistant tubes. Instead of the binocular tube mentioned, it is obviously also possible to provide a (video) image receiver by means of which a 3-dimensional image can be observed, for example.

It is also advantageous if the rotatable housing mentioned above which carries the interface for the assistant module surrounds the optical beam splitter device and this beam splitter device can be brought into its first or second position as specified by a rotary movement of the housing (for the purpose of a change of assistant). As the change of assistant involves rotating the housing through 180°, this rotation can be used to rotate at least some of the optical components of the beam splitter device. If for example only a 90° rotation of these optical components is needed, corresponding translation of the rotary movements is necessary. It should be emphasised once again that it is not absolutely essential for the rotatable housing to be mechanically coupled to the beam splitter device or its optical components. In fact, it is also conceivable for a 180° rotation of the housing with the assistant interface to be detected and then the beam splitter to be brought from its first position into its second position (or back again), for example by means of an own drive associated with the beam splitter device.

It is also advantageous if a fixed connection for a documentation module is mounted on the microscope housing. The fact, as the documentation beam path is again coupled out from the same (second) main beam path when there is a change of assistant, the documentation interface does not have to be of movable design but may be fixed to the microscope.

In an arrangement of this kind it is advantageous if the connection for the documentation module is arranged outside the area of rotation of the interface for the assistant module provided on the rotatable housing.

Without restricting the generalities, it will be assumed herein after that the coupled out assistant beam paths (in both positions of the beam splitter device) are located in a horizontal plane which itself is in a perpendicular position on the plane containing the two main beam paths of the microscope. The coupled out documentation beam path is assumed to lie in the same plane or in a horizontal plane parallel thereto.

Below is a description of two preferred embodiments of the invention, particularly the beam splitter device, while on the basis of the fundamental principles explained, the skilled man by combining features will be able to discover other possible solutions which fall within the scope of the present invention.

First of all, it is advantageous according to the first preferred embodiment if the beam splitter device has only two optical beam splitters each of which is arranged in one of the two main beam paths, particularly offset from one another in the direction of the microscope axis. The two beam splitters thus couple out an assistant and documentation beam path, respectively. As the direction of the coupled out assistant beam path is perpendicular to that of the coupled out documentation beam path, in case of a change of assistant the beam splitter which couples out the assistant beam path has only to be simply rotated through 180° about its own (central) axis which coincides with the corresponding main beam path. Thus the beam splitter which in the first position couples out the assistant beam path couples it out in the second position as well. The same applies analogously to the other beam splitter which couples out the documentation beam path, and is preferably arranged non-rotatably, so that the documentation interface can be mounted fixedly on the microscope. With a corresponding (1:1) transmission of the rotations, a rotation of the beam splitter or splitters, for example, particularly the beam splitter for the assistant beam path, may be coupled to a rotation of the housing which comprises the interface for the assistant module.

It is expedient and advantageous to arrange the two optical beam splitters each in one of the two main beam paths in such a way that they are displaced with respect to one another in the direction parallel to the axis of the microscope. Assuming that the two main beam paths lie in a vertically aligned plane, in such an arrangement of beam splitters for example the upper beam splitter can always decouple the documentation beam path from the second main beam path, whereas the lower beam splitter always decouples the documentation beam path from the first main beam path. Since the beam splitters are not adjacent to one another, but are arranged displaced with respect to one another, the assistant beam path can in both positions of the beam splitter device pass unhindered to the interface of an assistant module. If, on the other hand, the two beam splitters were arranged next to one another, then at least in one position of the beam splitter device the assistant beam path would have to be deflected around the beam splitter for the documentation beam path.

As already mentioned, it is particularly advantageous if for the changeover of the beam splitter device from the first position to the second position one of the two optical beam splitters, namely the one for decoupling the assistant beam path, can rotate by 180° about its own axis, which coincides with the corresponding main beam path. The rotation of the beam splitter device can be forcibly coupled to that of the relevant beam splitter. Thus, in this embodiment no further optical components except a beam splitter are moved (rotated and/or linearly displaced) in an assistant change. The documentation interface is fixedly associated with the documentation beam path decoupled from the other (second) main beam path. These are the two main distinguishing features compared to the earlier application DE 10 2006 050 846.7 already mentioned hereinbefore. On account of the smaller number of movable parts the manufacture and installation are significantly simplified and the costs are reduced.

In a second preferred embodiment the beam splitter device comprises four optical beam splitters, two of which are arranged in one of the two main beam paths. On account of the fact that beam splitters are arranged above one another in the direction of a main beam path, there is a light loss for the main observer. An advantage of such a solution may, however, be the fact that the changeover of the beam splitter device from its first position to the second position (and vice versa) can be effected by rotating all four optical beam splitters as one unit.

For example, it is advantageous if two beam splitters arranged in particular next to one another in different main beam paths each decouple an assistant beam path, the two lower (viewed from the object) beam splitters being for example used for this purpose. In the same way it is advantageous if the two other beam splitters arranged in particular next to one another in different main beam paths each decouple a documentation beam path. The two upper (viewed from the object) beam splitters can be used for this purpose. With such an arrangement an assistant beam path is consequently decoupled from each main beam path. The same applies in a similar way to the documentation beam path, where for the sake of simplicity in particular only one documentation beam path can actually be used.

In a first position of the beam splitter device the assistant beam path (at least from the first main beam path) is now guided to the assistant module, while the documentation beam path (at least from the second main beam path) is guided to the documentation module. In case of change of assistant, the same main beam paths are used for the decoupled assistant and documentation beam paths. For this purpose an arrangement is in particular useful in which the four optical beam splitters form one unit, which can be arranged so as to rotate 180° about the axis of the microscope for the changeover of the beam splitter device from the first position to the second position. This embodiment too thus has the advantage of a smaller number of movable parts, which in turn simplifies the production and installation and reduces costs.

Also both decoupled assistant beam paths can be used, for example to increase the brightness level and/or to permit stereoscopic observation. The same also applies in a similar way to the documentation beam path. If need be additional beam deflectors should however also be provided for this purpose. In any case, in the aforementioned second embodiment there still remains however the disadvantage of light loss still for the main observer.

The aforedescribed features of the invention can be used not only in the combination specified above, but also in other combinations or in isolation, without going beyond the scope of the invention.

Further objects, features and advantages of the present invention will become apparent from the detailed description of preferred embodiments that follows, when considered together with the accompanying figures of drawing.

BRIEF DESCRIPTION OF THE DRAWINGS

Various embodiments of the invention and their advantages are described in more detail hereinafter in conjunction with the accompanying drawings, in which.

DETAILED DESCRIPTION OF PREFERRED EMBODIMENTS

Figure 1:
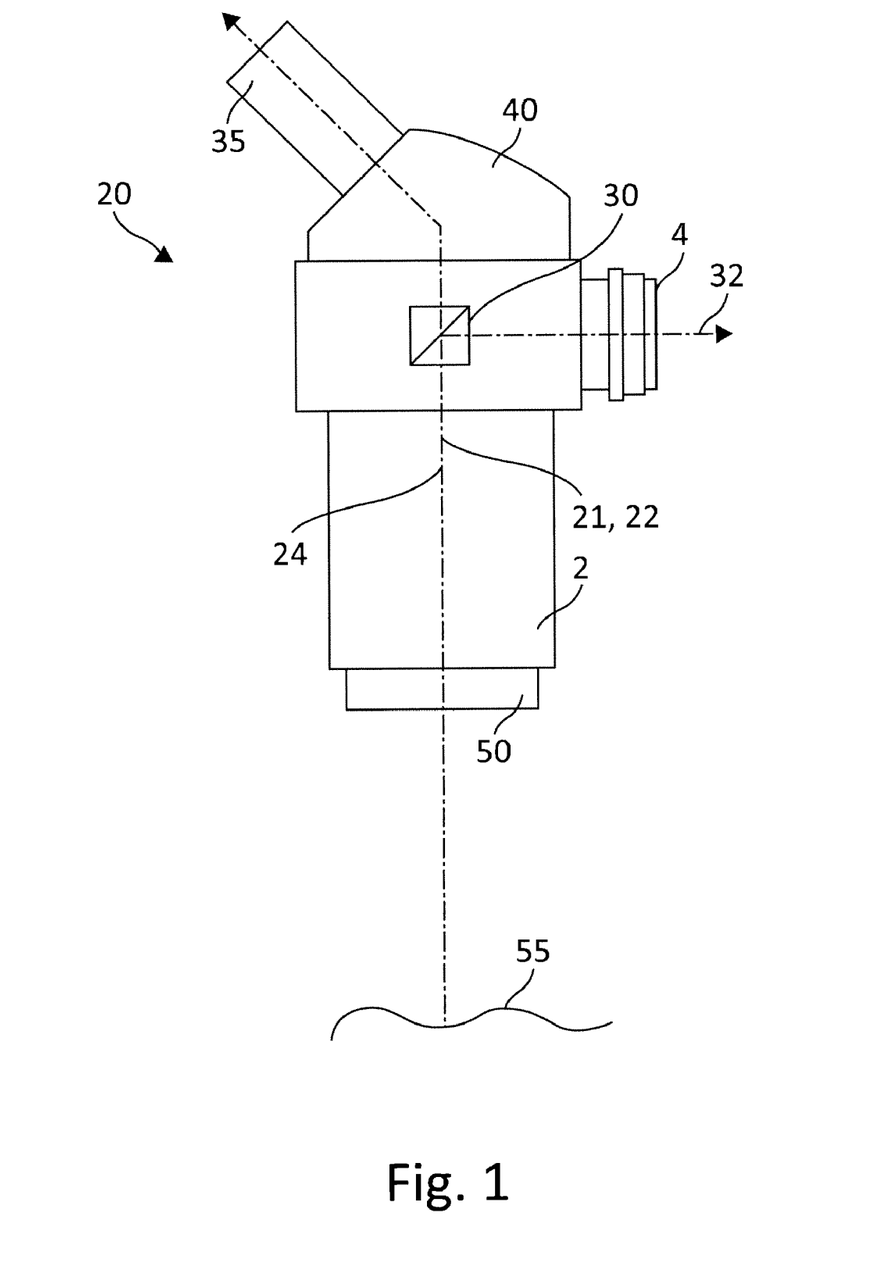
FIG. 1 shows diagrammatically in a side view the basic arrangement of a stereo microscope according to the invention.

FIG. 1 shows diagrammatically in a side view the basic arrangement of a stereo microscope 20 according to the invention. An object 55 located at the focus of the objective lens 50 of the stereo microscope 20 is imaged through a binocular tube 40 with two eyepieces 35 (in the side view only one of the eyepieces 35 is visible), this image being able to be observed by a main observer (for example a surgeon). Normally in such stereo microscopes 20 two channels of a magnification system, such as a zoom system or magnification changer, are arranged between the objective lens 50 and binocular tube 40 to provide a continuous or stepwise change in magnification. Since this arrangement is known per se, it will not be described in more detail hereinafter. The two optical channels of the magnification system are arranged in the microscope body 2 adjacent to one another in a plane perpendicular to the plane of the drawing. They define a first and a second main beam path 21 and 22 respectively. In these two main beam paths 21, 22 there is provided a beam splitter device 30, which decouples an assistant beam path 31 and a documentation beam path 32 from the main beam paths. In the example of implementation considered in FIG. 1, the documentation beam path 32 is decoupled in the direction of the rear side of the stereo microscope 20 and is guided to a connection 4 for the documentation. The beam splitter device 30 is in this case shown diagrammatically as a beam splitter. The assistant beam path 31 is decoupled perpendicularly to the documentation beam path 32, an interface for the assistant module being situated in a plane that runs perpendicular to the plane of the drawing, for example through the sketched beam splitter. The interface 6 for the assistant module is consequently situated on the left-hand or right-hand side of the microscope housing. 24 denotes the axis of the microscope, which in this case runs symmetrically between the two main beam paths 21, 22.

Figure 2:
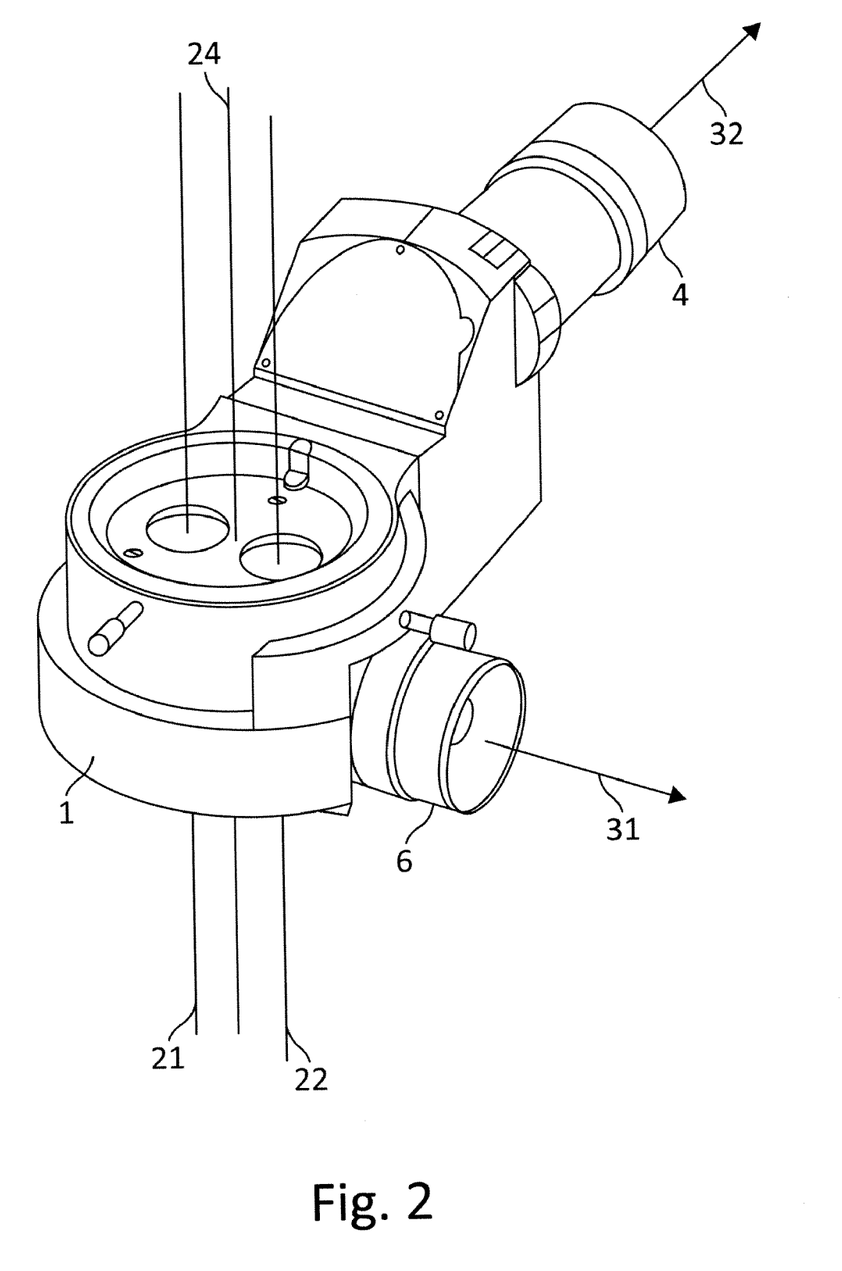
FIG. 2 shows perspectively a plan view of part of the stereo microscope according to FIG. 1, which contains the interface for the assistant module and for the documentation.

FIG. 2 shows perspectively a plan view of a part of the stereo microscope 20 according to FIG. 1, which contains the interface 6 for the assistant module and the connection 4 for the documentation. In the embodiment considered here the interface 6 for the assistant module is formed in a plane that contains the cross-section of the microscope body 2 and can swivel by at least 180° about the axis of the microscope 24. It is furthermore assumed that the connection 4 for the documentation is arranged fixed to the microscope and is centred relative to the two main beam paths 21, 22 in the illustrated manner. In this example the beam splitter device 30 (cf. FIG. 3) is moved from the first to the second position (or vice versa) by swiveling the interface 6 for the assistant module by 180°. In this changeover of the beam splitter device 30 from the first position to the second position (and vice versa) the parts of the beam splitter device 30 must be moved in such a way that the assistant beam path 31 decoupled from the first main beam path 31 is directed to the interface 6, rotated by 180°, for the assistant module, while the documentation beam path 32 decoupled from the second main beam path 22 is guided to the connection 4, connected to the microscope, for the documentation. The mechanism effecting this operation is described hereinafter with reference to FIG. 3.

Figure 3:
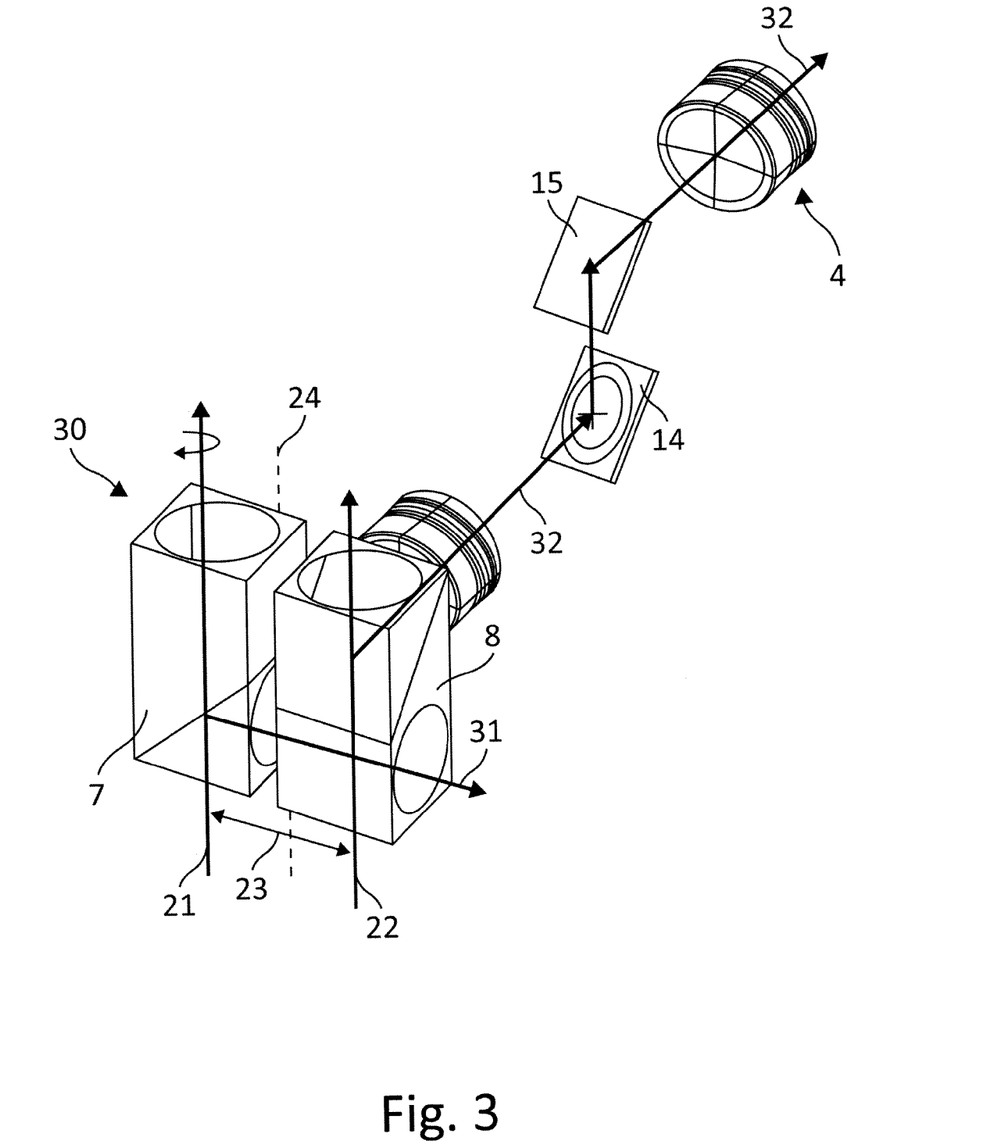
FIG. 3 shows a perspective detailed view of a first preferred embodiment with the beam splitter device in its first position.

FIG. 3 shows a particularly advantageous embodiment of a stereo microscope, in which a rotation of the housing 1 containing the interface 6 for the assistant module with a microscope-fixed connection 4 for the documentation effects a changeover of the beam splitter device 30 from a first position to a second position (cf. FIG. 2). FIG. 3 shows a diagrammatic, perspective view of the beam splitter device 30 as well as of the connection 4 for the documentation. Two beam splitters 7 and 8 are shown here, wherein in this embodiment the beam splitter 7 decouples the assistant beam path 31 from the first main beam path 21, while the beam splitter 8 decouples the documentation beam path 32 from the second main beam path 22. The two beam splitters 7 and 8 are not arranged adjacent to one another, but are arranged displaced in the direction of the axis of the microscope 24. In this way the decoupled assistant beam path 31 can bypass the beam splitter 8 for the documentation beam path unhindered if the assistant beam path 31 is decoupled in the direction illustrated in FIG. 3.

In the embodiment illustrated in FIG. 3 the first beam splitter 7 is mounted so as to be rotatable by (at least) 180°, whereas the other beam splitter 8 is arranged in a rotationally fixed manner. In a changeover of the beam splitter device from a first position to a second position, the beam splitter 7 is rotated by 180° about its axis, which lies on the axis of the main beam path 21. In this way the assistant beam path 31 is changed over from a laterally rightwards decoupled direction to a laterally leftwards decoupled direction. The decoupling for the documentation remains unaffected by this. The documentation beam path 32 is, regardless of a changeover of the beam splitter direction 30 from a first position to a second position, always decoupled from the second main beam path 22 in the manner illustrated in FIG. 3. FIG. 3 shows diagrammatically further optical components that are mounted in the connection 4 for the documentation. These include for example beam deflectors 14, 15, which deflect the decoupled documentation beam path to the interface for the documentation (camera or the like).

The embodiment illustrated in FIG. 3 has the advantage of a smaller number of movable parts, since only a single part, namely the beam splitter 7, has to be rotatable. All other parts can be fixedly mounted. A further advantage is the reduced light loss in the binocular tube 40 of the main observer, which is situated in the direction illustrated in FIG. 3 by the arrows on the main beam paths 21, 22. Assuming that the beam splitters each reflect or transmit 50% of the light, the main observer has available two observation channels (main beam paths 21 and 22) with 50% luminosity each, while the documentation and the assistant each likewise receive 50% of the original luminosity under monocular observation.

FIG. 4 shows in a perspective view a further embodiment of a beam splitter device 30 with four beam splitters.

Figure 4A:
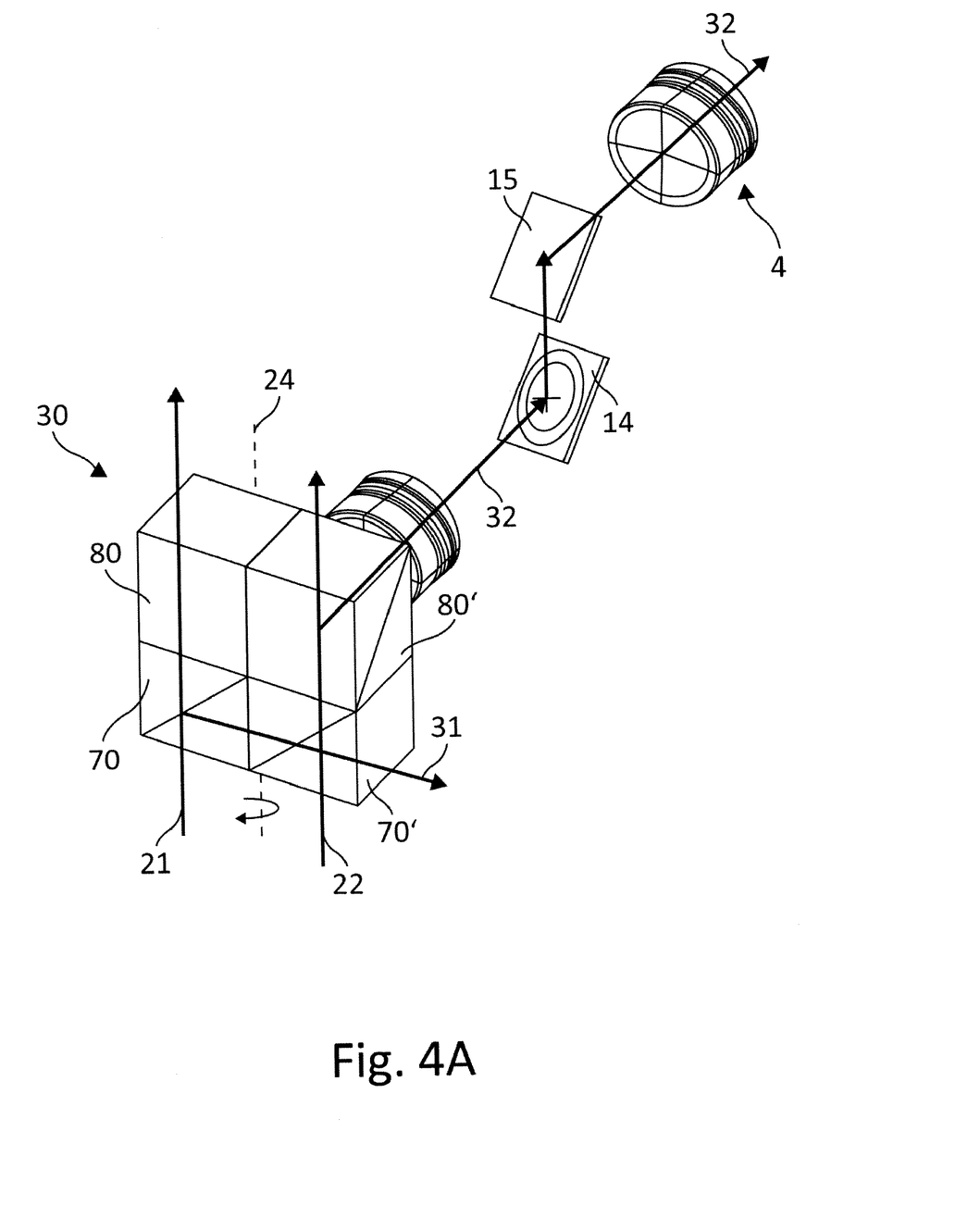
FIG. 4A shows a perspective detailed view of a second preferred embodiment with the beam splitter device in its first position.
Figure 4B:
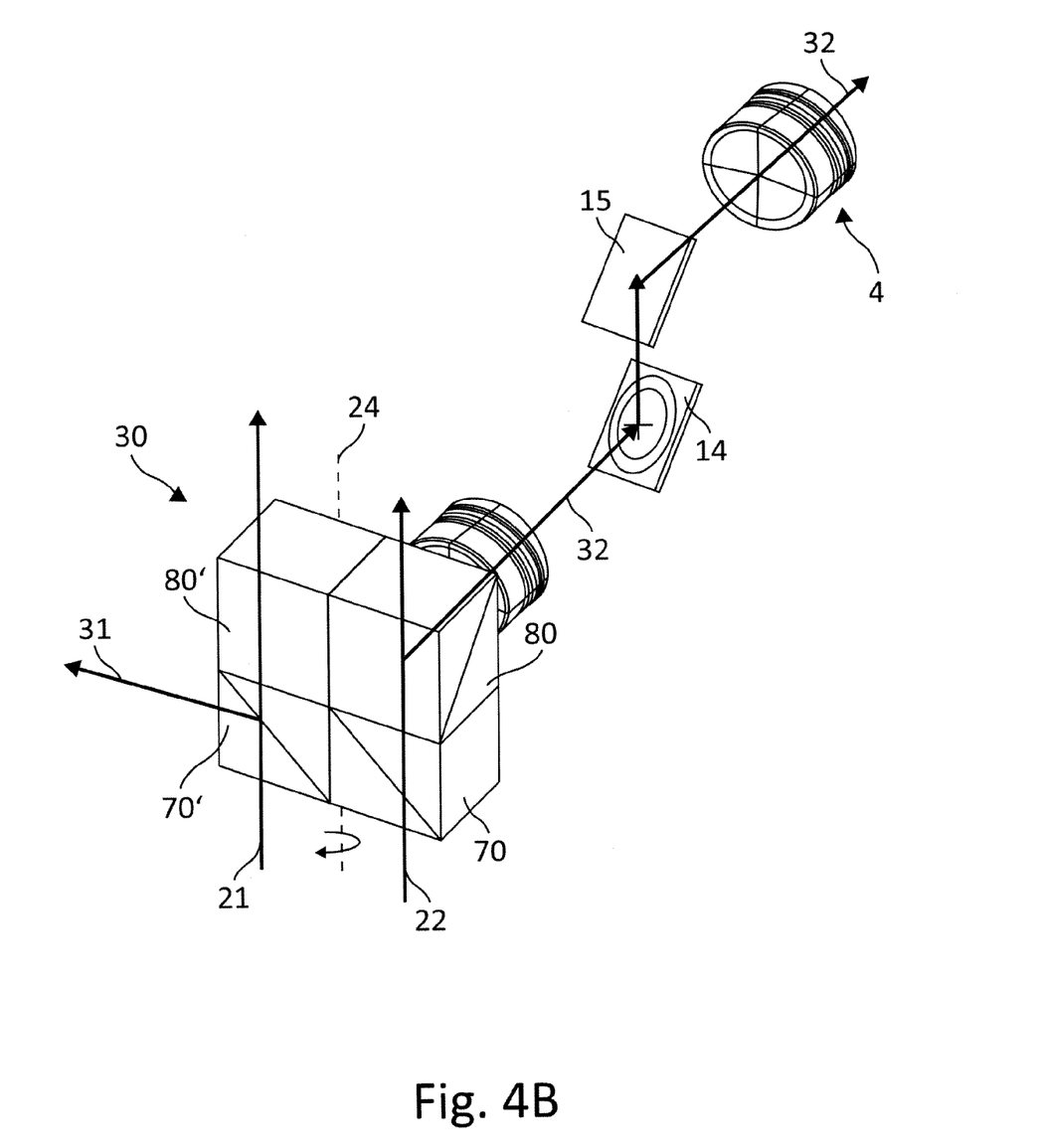
FIG. 4B shows a perspective detailed view of a second preferred embodiment with the beam splitter device in its second position.

FIGS. 4A and 4B are treated jointly hereinafter. In this example of implementation of the preferred second embodiment, as in the already discussed first embodiment, the connection 4 for the documentation is arranged fixed to the microscope. The decoupled documentation beam path 32 is again deflected by means of beam deflectors 14 and 15 to the connection 4 for the documentation. The decoupling of the documentation beam path 32 takes place again (only) from the second main beam path 22.

The beam splitter device 30 comprises in the present case four beam splitters 70, 70', 80, 80', in each case two beam splitters being arranged above one another in each of the two main beam paths 21 and 22. The beam splitters 70 and 70' are provided for the assistant beam path, the beam splitters 80 and 80' for the documentation beam path. In the illustrated embodiment the beam splitters 70 and 70' as well as 80 and 80' each lie adjacent to one another.

FIG. 4A shows the beam splitter device 30 in its first position, in this case the assistant beam path 31 being decoupled on the right-hand side. This decoupling takes place (at least) via the beam splitter 70, which is arranged in the first main beam path 21. On account of the symmetry relationships of the arrangement of the beam splitter device illustrated in FIG. 4A, in this example of implementation there is a further decoupling of an assistant beam path 31 from the second main beam path 22 by means of the beam splitter 70'. The documentation beam path 32 is in the present case decoupled by means of the beam splitter 80' from the second main beam path 22. For reasons of symmetry of the arrangement illustrated here, a further decoupling takes place on account of the beam splitter 80 arranged in the first main beam path 21. This decoupling is in the present case however not employed further, and is therefore not described in detail.

To summarise, it can be said that in the example of implementation according to FIG. 4A the assistant beam path 31 is decoupled from the first main beam path 21 (as well as from the second main beam path 22) and the documentation beam path 32 is decoupled (only) from the second main beam path 22.

By swivelling the housing 1 illustrated in FIG. 2 the interface 6 for the assistant module can be rotated by 180° (in the present case to the left). The beam splitter device 30 is thereby changed from its first position to the second position. This is accompanied by a corresponding 180° rotation of the unit consisting of the four beam splitters 70, 70', 80 and 80' about the axis of the microscope 24. The corresponding final position is shown in FIG. 4B.

As shown in FIG. 4B, the documentation beam path 32 is furthermore now decoupled from the second main beam path 22 by means of the beam splitter 80. The assistant beam path 31 is in turn decoupled from the first main beam path 21 by means of the beam splitter 70'. In addition a further (not shown) decoupling from the second main beam path 22 is effected here by means of the beam splitter 70.

The example of implementation of the preferred second embodiment of the invention illustrated in FIG. 4 has the advantage that the beam splitters are combined into one unit, which is designed so as to be able to rotate as such about the axis of the microscope 24, so that only a single part has to be movable (rotatable). This leads to the advantages already discussed hereinbefore.

The invention provides a stereo microscope with assistant and documentation output, which can advantageously be used in particular in surgery. The arrangement permits a smooth change of assistant, without any danger of collision with the document interface or with the main observation tube. The proposed arrangements (cf. first and second embodiments) are ergonomic and functional. The proposed rotatable housing for the assistant exchange with the obligatory involvement of the components of the beam splitter device 30, which on swivelling of the rotatable housing changes from its first position to the second position, permits an automatic change of assistant that is highly convenient for the user, and which moreover does not affect the image brightness or the image orientation. The proposed embodiments are relatively inexpensive to implement and do not require a four-beam microscope arrangement, which would involve disproportionately high costs.

The foregoing description of preferred embodiments of the invention has been presented for purposes of illustration and description only. It is not intended to be exhaustive or to limit the invention to the precise form disclosed, and modifications and variations are possible and/or would be apparent in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto and that the claims encompass all embodiments of the invention, including the disclosed embodiments and their equivalents.

LIST OF REFERENCE NUMERALS

1 rotatable housing
2 microscope housing
4 connection for documentation
6 assistant module interface
7 beam splitter, splitter prism
8 beam splitter, splitter prism
14, 15 beam deflectors 20 stereo microscope
21 first main beam path
22 second main beam path
23 stereo base
24 microscope axis
30 optical beam splitter device
31 decoupled assistant beam path
32 decoupled documentation beam path
35 eyepiece
40 binocular tube
50 objective lens
55 object
70, 70' beam splitter, splitter prism
80, 80' beam splitter, splitter prism

What is claimed is:

1. Stereo microscope comprising:
a first and a second main beam path for a main observer, the spacing of which defining a stereo base,
wherein an axis of the microscope extends through the middle of the stereo base parallel to the main beam paths,
an optical beam splitter device configured to produce an assistant beam path and a documentation beam path,
wherein a direction of the assistant beam path in a first position is rotated by 180° to a direction of the assistant beam path in a second position of the beam splitter device and the documentation beam path, which is decoupled, in both positions of the beam splitter device is in each case perpendicular to the assistant beam path, which is decoupled,
wherein in both the first and second positions of the beam splitter device the assistant beam path can in each case be decoupled from at least the first main beam path, wherein the assistant beam path is decoupled from the same, first main beam path in both the first and second positions of the beam splitter device, and
wherein the documentation beam path is in each case decoupled from at least the second main beam path,
wherein a fixed connection for a documentation module is mounted on a microscope housing, the documentation beam path being fixed in a direction from the optical beam splitter device to the fixed connection, the fixed connection being fixed relative to the axis of the microscope.

2. Stereo microscope according to claim 1, wherein a binocular tube and/or a connection for a documentation module is arranged downstream of the optical beam splitter device.

3. Stereo microscope according to claim 1, wherein an interface is provided for an assistant module, which is arranged in a housing that can rotate by at least 180° about the axis, of the microscope.

4. Stereo microscope according to claim 3, wherein the rotatable housing surrounds the beam splitter device and said beam splitter device can be brought into the first or second position by a rotational movement of the housing.

5. Stereo microscope according to claim 1, wherein the connection for the documentation module is arranged outside a range of rotation of an interface for an assistant module mounted on a rotatable housing, the assistant beam path being in a direction from the optical beam splitter device to the interface for the assistant module.

6. Stereo microscope according to claim 1, wherein the beam splitter device comprises two optical beam splitters, each of which are arranged in one of the two main beam paths.

7. Stereo microscope according to claim 6, wherein one of the two optical beam splitters is arranged so as to be rotatable by 180° about an axis of a main beam path.

8. Stereo microscope according to claim 7, wherein an other of the two optical beam splitters is arranged in a rotationally fixed manner.

9. Stereo microscope according to claim 6, wherein for a changeover of the beam splitter device from the first position to the second position, one of the two optical beam splitters is rotatable by 180° about an axis of a main beam path.

10. Stereo microscope according to claim 1, wherein the documentation beam path is decoupled from the same, second main beam path in both the first and second positions of the beam splitter device.

* * * * *